US00PP28048P2

(12) United States Plant Patent
Meulenbroek

(10) Patent No.: US PP28,048 P2
(45) Date of Patent: May 23, 2017

(54) STRAWBERRY PLANT NAMED 'YAMBU'

(50) Latin Name: *Fragaria×ananassa*
Varietal Denomination: Yambu

(71) Applicant: Egbertus Joseph Meulenbroek, Zetten (NL)

(72) Inventor: Egbertus Joseph Meulenbroek, Zetten (NL)

(73) Assignee: Fresh Forward Holding B.V., Eck en Wiel (NL)

( * ) Notice: Subject to any disclaimer, the term of this patent is extended or adjusted under 35 U.S.C. 154(b) by 0 days.

(21) Appl. No.: 14/757,312

(22) Filed: Dec. 15, 2015

(51) Int. Cl.
*A01H 5/08* (2006.01)

(52) U.S. Cl.
USPC ..... Plt./208

(58) Field of Classification Search
USPC ..... Plt./208
See application file for complete search history.

*Primary Examiner* — Annette Para
(74) *Attorney, Agent, or Firm* — C. A. Whealy

(57) ABSTRACT

A new and distinct cultivar of Strawberry plant named 'Yambu', characterized by its compact and semi-upright plant habit; moderately vigorous growth habit; uniform fruit ripening; large conical fruits that are glossy and orange red in color; pleasant fruit aroma and taste; fruits with relatively few seeds; excellent fruit postharvest longevity; and relative resistance to *Botrytis cinerea* and *Phytophthora cactorum.*

3 Drawing Sheets

Botanical designation: *Fragaria×ananassa.*
Cultivar denomination: 'YAMBU'.

BACKGROUND OF THE INVENTION

The present Invention relates to a new and distinct cultivar of Strawberry plant, botanically known as *Fragaria×ananassa* and hereinafter referred to by the name 'Yambu'.

The new Strawberry plant is a product of a planned breeding program conducted by the Inventor in Wageningen and Elst, Gelderland, The Netherlands. The objective of the breeding program was to develop new early-ripening Strawberry plants with good fruit quality, ease of harvesting, good postharvest longevity and resistance to pathogens.

The new Strawberry plant originated from a cross-pollination made by the Inventor in 2001 in Wageningen, The Netherlands of a proprietary Strawberry selection identified as code name E1991-023, not patented, as the female, or seed, parent with the Strawberry 'Honeoye', not patented, as the male, or pollen, parent. The new Strawberry plant was discovered and selected by the Inventor as a single plant from within the progeny of the stated cross-pollination in a controlled environment in Elst, Gelderland, The Netherlands during the summer of 2003.

Asexual reproduction of the new Strawberry plant by runner cuttings in a controlled environment at Elst, Gelderland, The Netherlands since the autumn of 2003, has shown that the unique features of this new Strawberry plant are stable and reproduced true to type in successive generations of asexual reproduction.

SUMMARY OF THE INVENTION

Plants of the new Strawberry have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Yambu'. These characteristics in combination distinguish 'Yambu' as a new and distinct Strawberry plant:

1. Compact and semi-upright plant habit.
2. Moderately vigorous growth habit.
3. Uniform fruit ripening.
4. Large conical fruits that are glossy and orange red in color.
5. Pleasant fruit aroma and taste.
6. Fruits with relatively few seeds.
7. Excellent fruit postharvest longevity.
8. Relatively resistant to *Botrytis cinerea* and *Phytophthora cactorum.*

Plants of the new Strawberry differ from plants of the female parent selection in the following characteristics:

1. Plants of the new Strawberry produce fruit earlier than plants of the female parent selection.
2. Fruits of plants of the new Strawberry are glossier than fruits of plants of the female parent selection.
3. Fruits of plants of the new Strawberry have fewer seeds than fruits of plants of the female parent selection.

Plants of the new Strawberry differ from plants of the male parent, 'Honeoye', in the following characteristics:

1. Plants of the new Strawberry produce fruit for a longer period of time than plants of 'Honeoye'.
2. Fruits of plants of the new Strawberry are larger than fruits of plants of 'Honeoye'.
3. Fruits of plants of the new Strawberry are glossier than fruits of plants of 'Honeoye'.
4. Fruits of plants of the new Strawberry have fewer seeds than fruits of plants of 'Honeoye'.

Plants of the new Strawberry can be compared to plants of Strawberry 'Sonata', disclosed in U.S. Plant Pat. No. 18,000. In side-by-side comparisons, plants of the new Strawberry differed primarily from plants of 'Sonata' in the following characteristics:

1. Plants of the new Strawberry are taller than plants of 'Sonata'.

2. Plants of the new Strawberry produce fruit earlier than plants of 'Sonata'.
3. Fruits of plants of the new Strawberry are darker red in color than fruits of plants of 'Sonata'.
4. Fruits of plants of the new Strawberry are glossier than fruits of plants of 'Sonata'.
5. Fruits of plants of the new Strawberry have fewer seeds than fruits of plants of 'Sonata'.

BRIEF DESCRIPTION OF THE PHOTOGRAPHS

The accompanying colored photographs illustrate the overall appearance of the new Strawberry plant showing the colors as true as it is reasonably possible to obtain in colored reproductions of this type. Colors in the photographs may differ slightly from the color values cited in the detailed botanical description which accurately describe the colors of the new Strawberry plant.

The photograph on the first sheet is a side perspective view of a typical fruiting plant of 'Yambu' grown in a container in a hydroponic system.

The photograph on the second sheet is a close-up view of typical fully opened flowers and a typical flower with a developing fruit of 'Yambu'.

The photograph on the third sheet is a close-up view of typical developing and developed fruits of 'Yambu'.

DETAILED BOTANICAL DESCRIPTION

The aforementioned photographs, following observations and measurements describe plants grown in 2.5-liter containers during the spring in a glass-covered greenhouse in Eck en Wiel, The Netherlands and under cultural practices typical of commercial Strawberry production. During the production of the plants, day temperatures ranged from 12° C. to 23° C. and night temperatures ranged from 8° C. to 12° C. Plants were 2.5 months old when the photographs were taken and plants were 3.5 months old when the description was taken. In the following description, color references are made to The Royal Horticultural Society Colour Chart, 2001 Edition, except where general terms of ordinary dictionary significance are used.

Botanical classification: *Fragaria×ananassa* 'Yambu'.

Parentage:

*Female, or seed, parent*.—Proprietary seedling selection of *Fragaria×ananassa* identified as code name E1991-023, not patented.

*Male, or pollen, parent*.—*Fragaria×ananassa* 'Honeoye', not patented.

Propagation:

*Type*.—By runner cuttings.

*Time to initiate roots, summer*.—About one to four days at soil temperatures about 15° C.

*Time to produce a rooted young plant, summer*.—About two weeks at soil temperatures ranging from 18° to 20° C.

*Root description*.—Thick to medium in thickness, fibrous; typically creamy white to white in color, actual color of the roots is dependent on substrate composition, water quality, fertilizer type and formulation, substrate temperature and physiological age of roots.

*Rooting habit*.—Freely branching; dense.

Plant description:

*Plant and growth habit*.—Perennial; compact and semi-upright plant habit; overall plant shape, flat globose; leaves basal; moderately vigorous growth habit.

*Plant height*.—About 35 to 40 cm.

*Plant diameter*.—About 30 to 35 cm.

Leaf description:

*Arrangement*.—Basal rosette; compound with typically three leaflets per leaf.

*Leaflet length*.—About 7 to 10 cm.

*Leaflet width*.—About 6 to 9 cm.

*Leaflet shape*.—Broadly ovate.

*Leaflet apex*.—Obtuse to acute.

*Leaflet base*.—Obtuse to rounded.

*Leaflet margin*.—Serrated to lobed.

*Leaflet texture, upper surface*.—Pubescent.

*Leaflet texture, lower surface*.—Pubescent, rough.

*Leaflet venation*.—Pinnate.

*Leaflet color*.—Developing leaflets, upper surface: Close to 137B. Developing leaflets, lower surface: Close to 138A. Fully expanded leaflets, upper surface: Close to between 137B and 139A; venation, close to 144D. Fully expanded leaflets, lower surface: Close to 138A; venation, close to 144D.

*Petioles*.—Length: About 9 to 15 cm. Diameter: About 2.5 to 5 mm. Texture, upper and lower surfaces: Pubescent. Color, upper and lower surfaces: Close to 145A.

Flower description:

*Flower form and flowering habit*.—Rotate flowers arranged singly at lateral apices; flowers held at the foliar plane.

*Fragrance*.—None detected.

*Natural flowering season*.—Plants flower in late April to early May in The Netherlands.

*Flower diameter*.—About 2.5 to 3.5 cm.

*Flower depth (height)*.—About 5 mm to 10 mm.

*Petals*.—Arrangement: Single whorl of five or six petals; petals imbricate. Length: About 4 mm to 7 mm. Width: About 4 mm to 7 mm. Shape: Round. Apex: Rounded. Base: Attenuate. Margin: Entire. Texture, upper and lower surfaces: Smooth, glabrous; satiny. Color: When opening and fully opened, upper surface: Close to 155D. When opening and fully opened, lower surface: Close to 155D.

*Sepals*.—Arrangement and calyx description: Single whorl of eight to twelve sepals; calyx, star-shaped; sepals are orientated upwards from the fruit. Length: About 5 mm to 8 mm. Width: About 3 mm to 5 mm. Shape: Lanceolate to ovate. Apex: Acute. Base: Fused. Margin: Entire. Texture, upper and lower surfaces: Pubescent. Color, upper and lower surfaces: Close to 137A.

*Peduncles*.—Length: About 7 cm to 10 cm. Diameter: About 1 mm to 2 mm. Strength: Strong. Texture: Pubescent. Color: Close to 144B.

*Pedicels*.—Length: About 2 cm to 5 cm. Diameter: About 1 mm to 2 mm. Strength: Strong. Texture: Pubescent. Color: Close to 144B.

*Reproductive organs*.—Stamens: Quantity per flower: About 25. Anther length: About 2 mm. Anther shape: Lanceolate to elliptic. Anther color: Close to 14B. Pollen amount: Abundant. Pollen color: Close to 15C. Pistils: Quantity per flower: About 30. Pistil length: About 1 mm to 2 mm. Stigma shape: Rounded. Stigma color: Close to 5A. Fruits: Natural fruiting season: Relatively early and long fruiting season, plants develop fruit during June and July in The Netherlands. Postharvest longevity: About eight days. Length: About 3 cm to 6 cm. Diameter: About 3 cm to 6 cm. Shape: Conical. Typical fruit weight per fruit: About 18 g to 19 g. Observed fruit weight per fruit: About 19 g to 20 g. Typical fruit weight per plant: About 900 g. Observed fruit weight per plant: About 1 kg. Firmness: Moderately firm. Fragrance, taste: Pleasant; good balance between sweetness and acidity. Luster: Glossy. Surface unevenness: Smooth, Color, surface: Close to 34A. Color, flesh: Close to between N34B and 33A. Seed density: Relatively low. Achene position: Level with surface. Achene color: Variable, close to 154A and 34B.

Disease and pest resistance: Plants of the new Strawberry have been observed to be resistant to *Botrytis cinerea* and *Phytophthora cactorum* and to be somewhat resistant to *Podosphaera aphanis* (formerly known as *Sphaerotheca macularis*). Plants of the new Strawberry have not been observed to be resistant to pests and other pathogens common to Strawberry plants.

It is claimed:

1. A new and distinct Strawberry plant named 'Yambu' as illustrated and described.

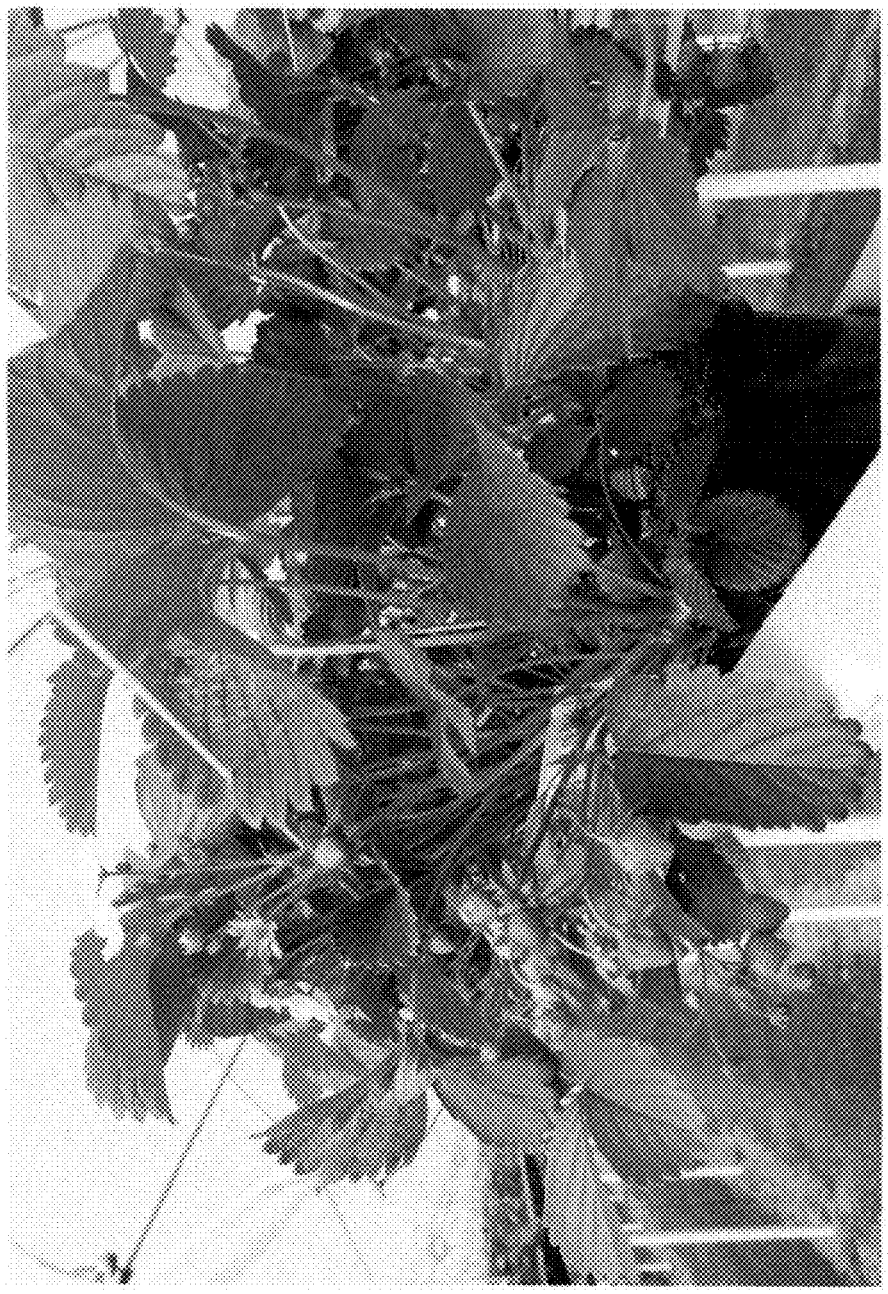

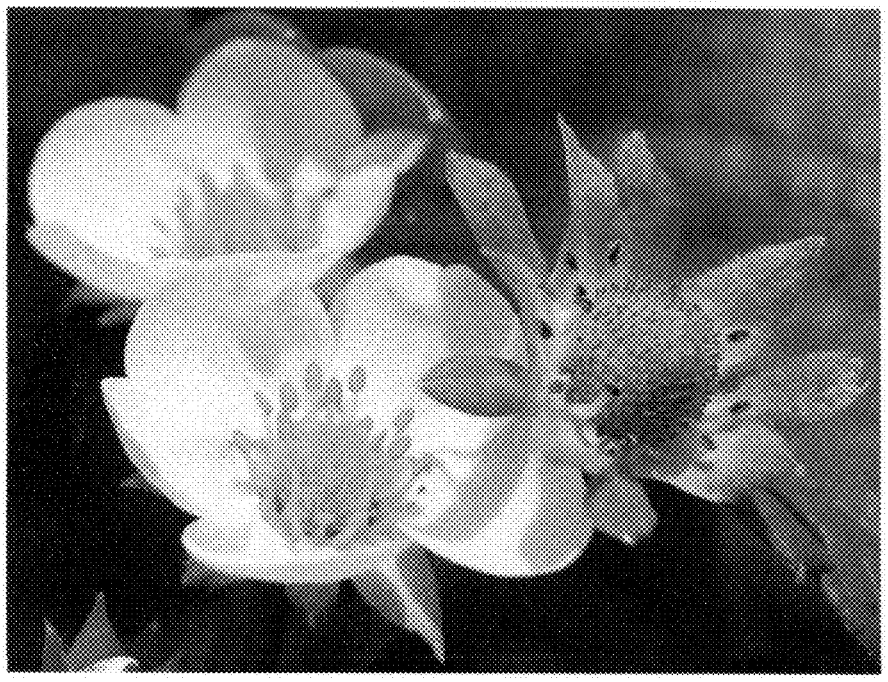

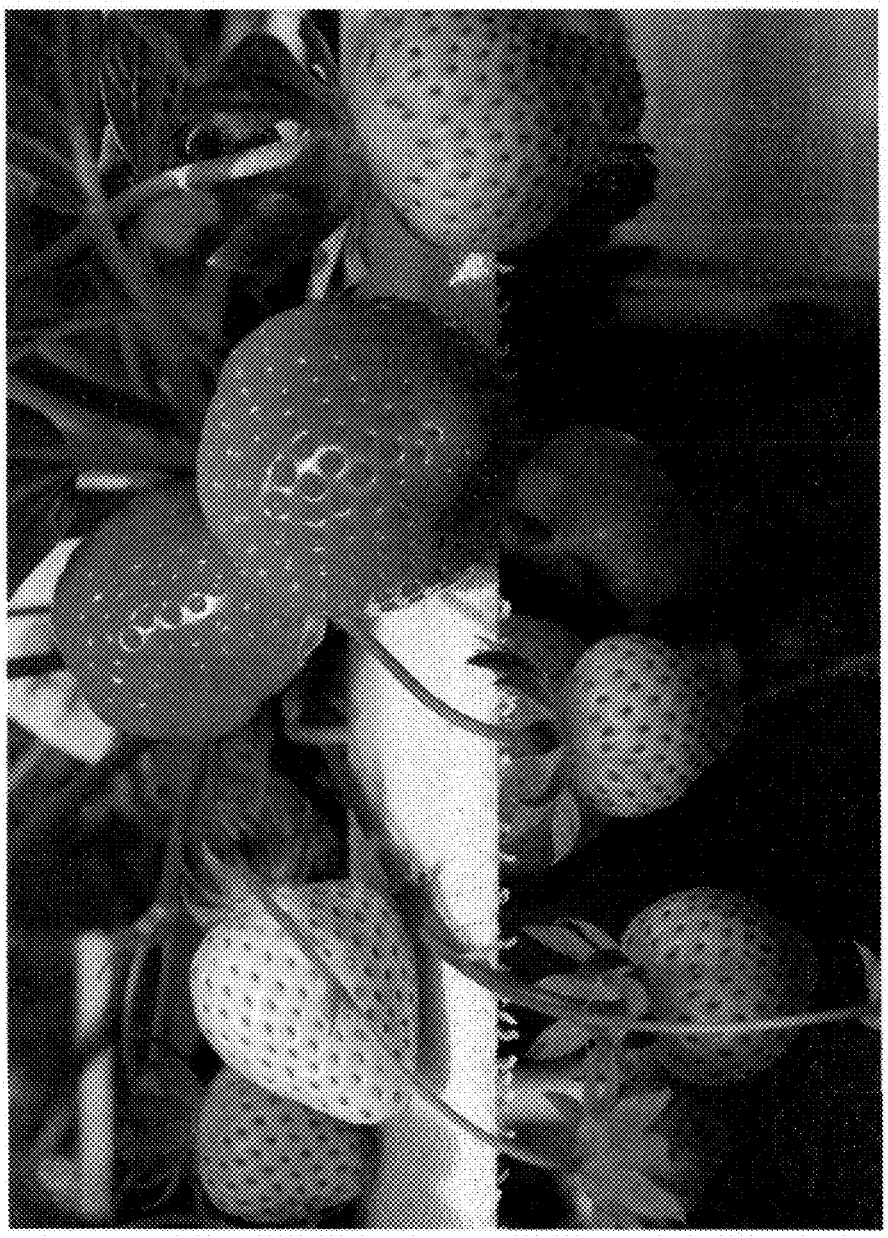

* * * * *